United States Patent
Coull et al.

(10) Patent No.: US 7,985,221 B2
(45) Date of Patent: Jul. 26, 2011

(54) EXTERNAL FIXATOR

(75) Inventors: Thomas Coull, Rancho Palos Verdes, CA (US); Lon S. Weiner, Rumson, NJ (US)

(73) Assignee: Millennium Medical Technologies, Inc., Plymouth, MN (US)

( * ) Notice: Subject to any disclaimer, the term of this patent is extended or adjusted under 35 U.S.C. 154(b) by 659 days.

(21) Appl. No.: 11/737,748

(22) Filed: Apr. 20, 2007

(65) Prior Publication Data

US 2008/0021451 A1    Jan. 24, 2008

Related U.S. Application Data

(60) Provisional application No. 60/793,590, filed on Apr. 20, 2006.

(51) Int. Cl.
*A61B 17/00* (2006.01)
*A61F 4/00* (2006.01)
*A61F 5/04* (2006.01)

(52) U.S. Cl. ............... 606/54; 606/57; 606/58; 600/210; 600/222; 600/225

(58) Field of Classification Search ............... 606/54–60, 606/279, 282, 90, 105; 600/208, 210, 214–219, 600/222–225
See application file for complete search history.

(56) References Cited

U.S. PATENT DOCUMENTS

| | | | |
|---|---|---|---|
| 2,333,033 A | 10/1943 | Mraz | |
| 2,393,694 A | 1/1946 | Kirschner | |
| 3,965,890 A * | 6/1976 | Gauthier | 600/215 |
| 4,548,199 A | 10/1985 | Agee | |
| 4,611,586 A | 9/1986 | Agee et al. | |
| 4,628,919 A | 12/1986 | Clyburn | |
| 4,662,365 A | 5/1987 | Gotzen et al. | |
| 4,730,608 A | 3/1988 | Schlein | |
| 4,848,327 A | 7/1989 | Perdue | |
| 4,889,111 A | 12/1989 | Ben-Dov | |
| 4,922,896 A | 5/1990 | Agee et al. | |
| 5,087,258 A | 2/1992 | Schewior | |
| 5,122,140 A | 6/1992 | Asche et al. | |
| 5,139,500 A | 8/1992 | Schwartz | |
| 5,527,309 A | 6/1996 | Shelton | |
| 5,562,661 A | 10/1996 | Yoshimi et al. | |
| 5,571,103 A | 11/1996 | Bailey | |
| 5,620,442 A | 4/1997 | Bailey et al. | |
| 5,658,283 A | 8/1997 | Huebner | |
| 5,662,649 A | 9/1997 | Huebner | |
| 5,683,389 A | 11/1997 | Orsak | |
| 5,697,934 A | 12/1997 | Huebner | |
| 5,810,814 A | 9/1998 | Newson | |

(Continued)

*Primary Examiner* — Todd E Manahan
*Assistant Examiner* — Christina Negrelli
(74) *Attorney, Agent, or Firm* — Shewchuk IP Services, LLC; Jeffrey D. Shewchuk (57) ABSTRACT

An external fixator for treating a fracture of a long bone has six extension arms which are extendable out of and retractable into a main body. The six extension arms are arranged into two sets of three out opposing sides of the main body, with each set of three extension arms being able to support a fixation ring. Each extension arm is pivotable at a joint and extendable so as to allow the ring to be set at a wide range of angular positions relative to the main body. The three extension arms and the ring each define a wrap angle about the axis of the long bone being treated. The longitudinal position of each extension arm can be changed either with a coarse adjustment capability or with a fine adjustment capability, with the coarse adjustment capability being through rotation of a thumb wheel.

12 Claims, 6 Drawing Sheets

U.S. PATENT DOCUMENTS

| | | | |
|---|---|---|---|
| 5,827,283 A | 10/1998 | Groiso et al. | |
| 5,897,555 A | 4/1999 | Clyburn et al. | |
| 5,968,046 A | 10/1999 | Castleman | |
| 5,989,255 A | 11/1999 | Pepper et al. | |
| 6,056,748 A | 5/2000 | Weiner | |
| 6,099,529 A | 8/2000 | Gertzman et al. | |
| 6,123,704 A | 9/2000 | Hajianpour | |
| 6,162,222 A * | 12/2000 | Poka et al. | 606/54 |
| 6,162,225 A | 12/2000 | Gertzman et al. | |
| 6,171,309 B1 | 1/2001 | Huebner | |
| 6,238,417 B1 | 5/2001 | Cole | |
| 6,283,964 B1 * | 9/2001 | Weiner | 606/55 |
| 6,355,037 B1 | 3/2002 | Crosslin et al. | |
| 6,652,523 B1 * | 11/2003 | Evrard et al. | 606/54 |
| 6,652,524 B1 | 11/2003 | Weiner | |
| 6,746,448 B2 | 6/2004 | Weiner et al. | |
| 6,918,910 B2 * | 7/2005 | Smith et al. | 606/60 |
| 7,029,472 B1 * | 4/2006 | Fortin | 606/60 |
| 7,507,240 B2 * | 3/2009 | Olsen | 606/59 |
| 7,615,051 B2 * | 11/2009 | Hamel | 606/56 |
| 2002/0010465 A1 * | 1/2002 | Koo et al. | 606/57 |
| 2007/0038217 A1 * | 2/2007 | Brown et al. | 606/57 |
| 2007/0073111 A1 * | 3/2007 | Bass | 600/215 |
| 2010/0042102 A1 * | 2/2010 | Hamel | 606/54 |

* cited by examiner

EXTERNAL FIXATOR

CROSS-REFERENCE TO RELATED APPLICATION(S)

This application claims priority from Provisional Application No. 60/793,590, filed Apr. 20, 2006.

BACKGROUND OF THE INVENTION

The present invention relates to the field of medical devices, and particularly to the design and manufacture of external fixation systems. External fixators are used during healing of tissue and particularly during healing of a fractured bone when it is desired to support two bone portions in a fixed position relative to one another during surgery or during healing.

The prior art contains many different types of external bone fixator devices which are used for setting various bone fractures. Many external bone fixator devices employ transcutaneous pins (e.g., K-wires), stakes, screws or other types of bone fasteners, which are secured in the bone or bone fragments on opposing sides of the fracture site. The pins are then secured to an external splint device. The external splint device may use various articulations to adjust its position relative to the bone fasteners. During the fixation surgery, the bone pieces at the fracture may be realigned by the surgeon. The various articulations in the external splint device may assist the surgeon in realigning the bone pieces. Once the external splint device is secured to the bones and the bone pieces are in the desired alignment positions, the articulations in the fixator are locked in place to maintain the bone alignment for a healing duration. Examples of external fixators include the devices and methods taught in U.S. Pat. Nos. 6,056,748, 6,283,964, 6,652,524, 6,746,448 and pending application Ser. No. 10/699,313, all incorporated by reference.

There is a need for improvement in external fixator devices. Many current external fixation systems have a frame which becomes unstable if it is expanded or lengthened. Conversely, if stability of such prior art designs is maximized, the frame is often too short or otherwise unacceptable for correction of the problem. Multiple parts are necessary to allow many prior art frames to be fully functional, the various parts may not be available or may not work well together. Many current external fixation systems include rings, wires, rods and pins which overly obscure the fracture site and create access problems.

Fixator devices need to be strong, rigid and durable, to withstand any forces or inadvertent blows to which the fracture site is subjected. Fixator devices should be lightweight, so as to movable by the patient without extreme difficulty. Fixator devices should be reasonable in manufacturing cost and difficulty. Fixator devices should facilitate a wide range of surgical techniques, to permit the surgeon to best adapt to the particular fracture and to provide the best mode of healing.

BRIEF SUMMARY OF THE INVENTION

The present invention is an extendable external fixator, having an extension arm extending out of a main body. The longitudinal position of the extension arm can be changed either with a coarse adjustment capability or with a fine adjustment capability, with the fine adjustment capability in the preferred embodiment being through rotation of a thumb wheel. In one aspect, the external fixator can be used with a ring supported by three extension arms, each extension arm being pivotable at a joint and extendable so as to allow the ring to be set at a wide range of angular positions relative to the main body. In another aspect, each pair of extension arm shafts is disposed in an abutting relationship in the main body such that the extension arm shafts extend or retract out opposing sides of the main body.

While the above-identified drawing figures set forth preferred embodiments, other embodiments of the present invention are also contemplated, some of which are noted in the discussion. In all cases, this disclosure presents the illustrated embodiments of the present invention by way of representation and not limitation. Numerous other minor modifications and embodiments can be devised by those skilled in the art which fall within the scope and spirit of the principles of this invention.

DETAILED DESCRIPTION

Figure 1:
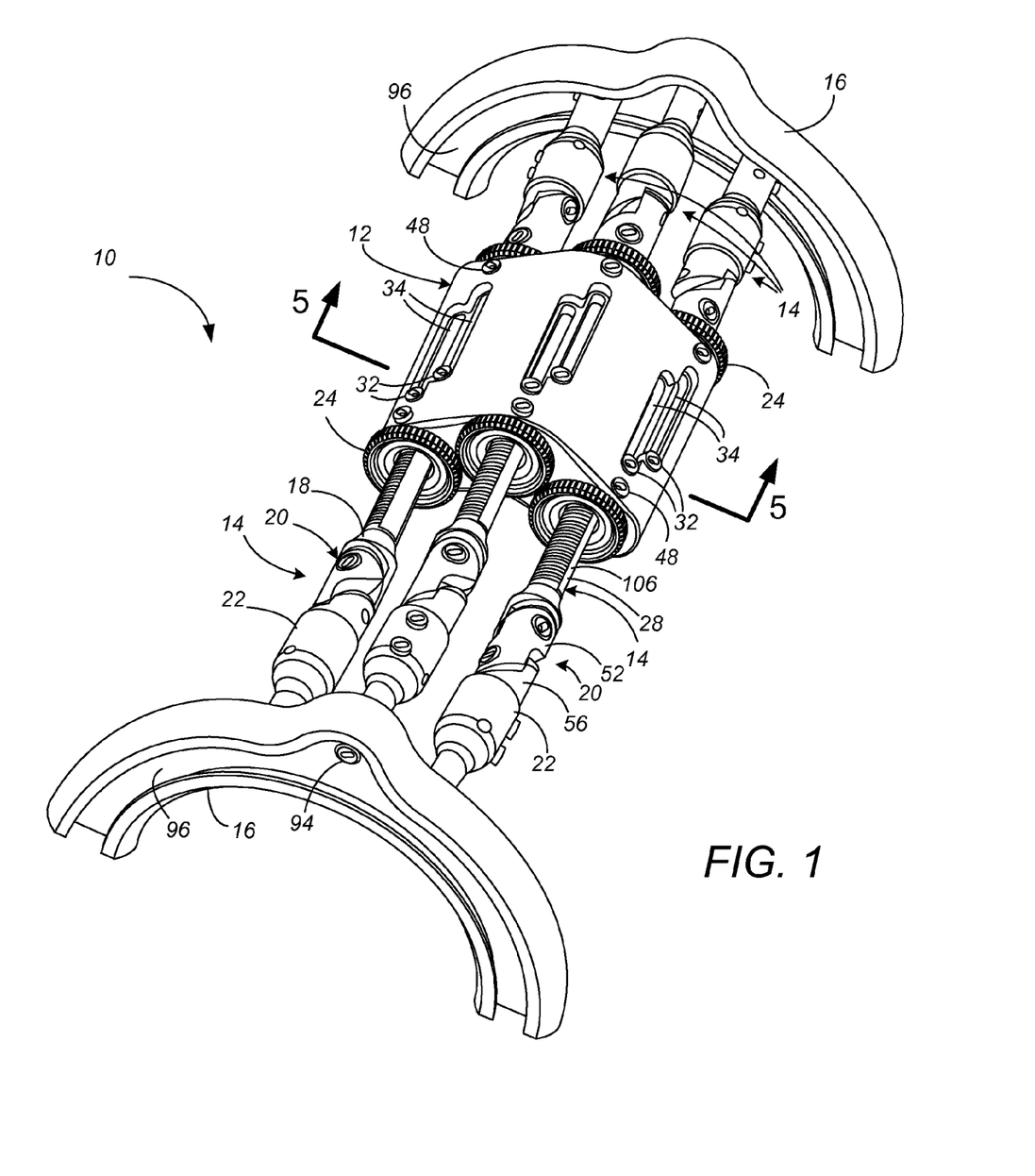
FIG. 1 is a perspective view of one preferred embodiment of an external fixator in accordance with the present invention.

A preferred embodiment of an external fixator 10 in accordance with the present invention is shown in FIG. 1. The external fixator 10 primarily includes a main body 12, six extension arms 14, and two fixation rings 16, each ring 16 supported by three of the extension arms 14.

Figure 2:
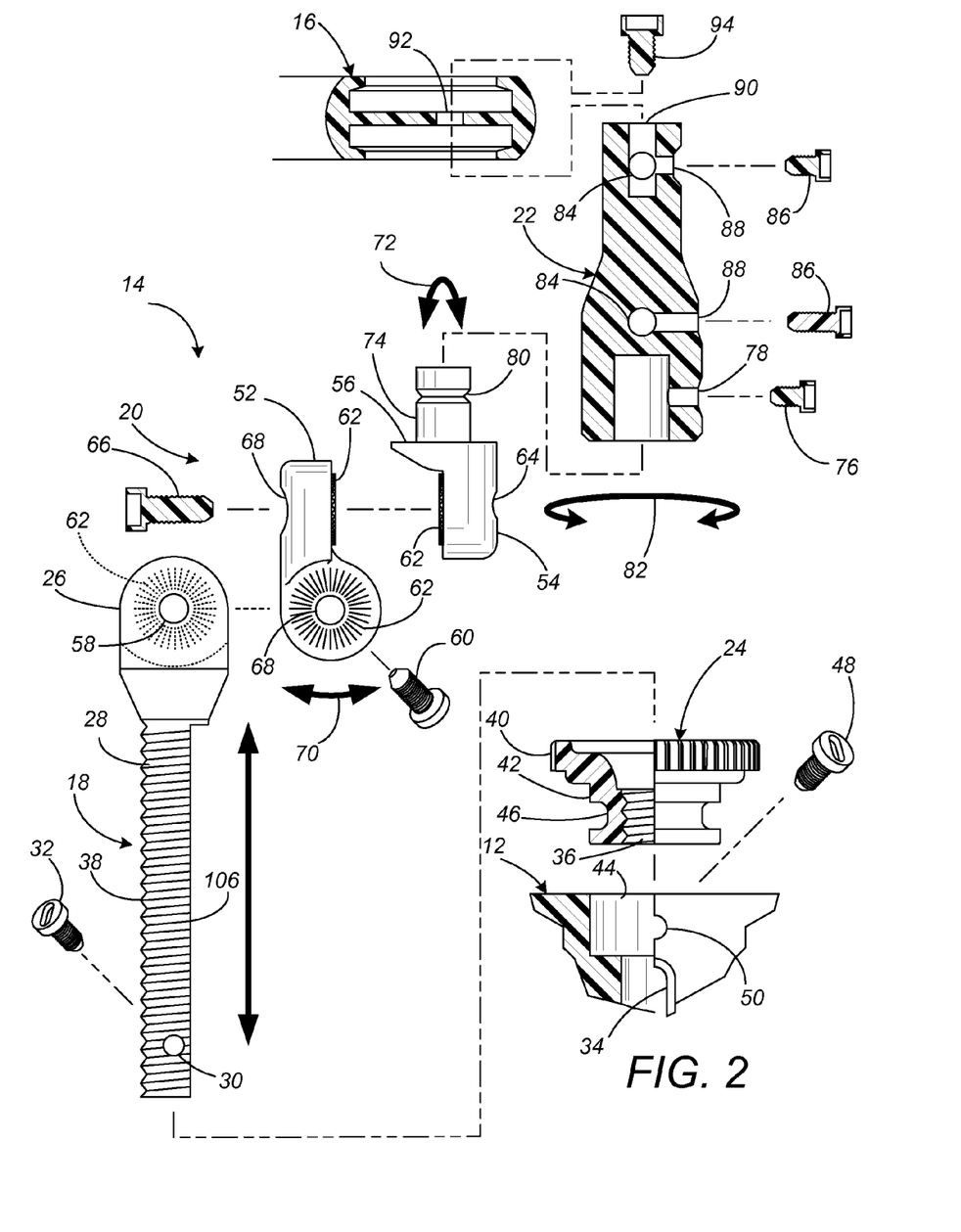
FIG. 2 is an exploded side view of one of the extension arms of the external fixator of FIG. 1, with the pin holder and fixation ring shown in cross-section and the main body and adjustment thumb wheel shown partially in cross-section.

An exploded side view of an extension arm 14 is shown in FIG. 2. Each extension arm 14 includes a rod member 18 which is movable longitudinally in and out from the main body 12. Each extension arm 14 also includes an articulating joint 20, followed by a pin holder or other configuration of minor body 22. The longitudinal position of each arm 14 relative to the main body 12 is subject to a coarse adjustment and a fine adjustment, with the fine adjustment of each arm 14 controlled by a thumb wheel 24.

Figures 3, 4:
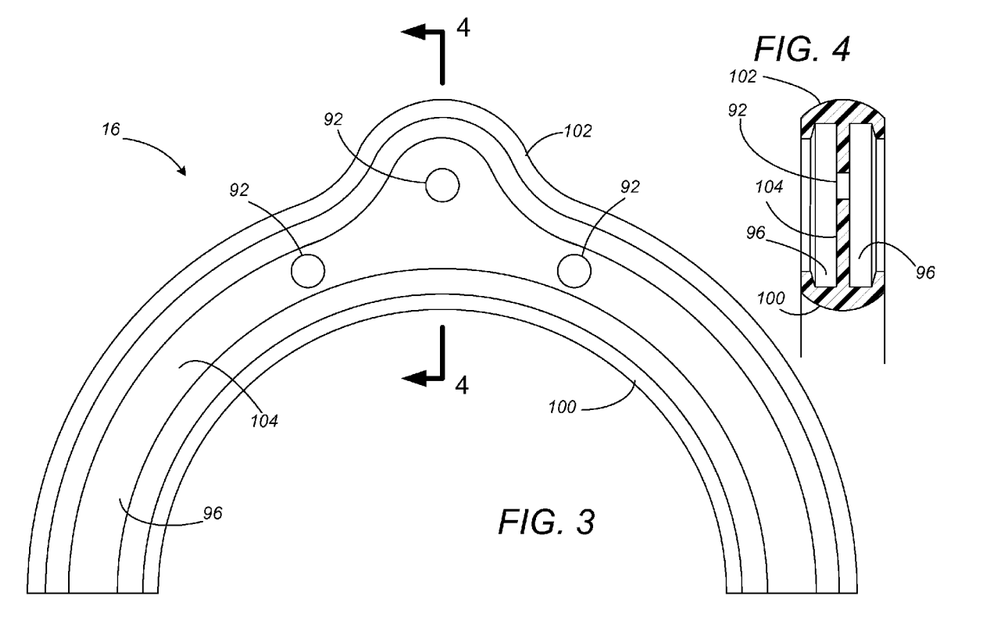
FIG. 3 is a side view of the fixation ring of the external fixator of FIG. 1.
FIG. 4 is a cross-sectional view taken of the fixation ring of FIG. 3 taken along lines 4-4.

The rod member 18 includes a head 26 and a shaft 28. The length of the shaft 28 in part defines the length of travel of the longitudinal adjustment of the extension arm 14. The shaft 28 includes a threaded hole 30 for receiving a threaded slide tightening screw 32. When received in the threaded hole 30, the slide tightening screw 32 mates into a slide slot 34 as best shown in FIGS. 1 and 4, and travels with the rod member 18 as the longitudinal position of the extension arm 14 is adjusted into or out of the main body 12. In the preferred embodiment, each slide slot 34 in the main body 12 is about 55 mm long, and each rod member 18 has a shaft length of about 72 mm. With the slide tightening screw 32 loosely in place, the extension arm 14 is movable from a fully retracted position, wherein the shaft 28 is fully within the main body 12 and the slide tightening screw 32 is at a proximal end of its slide slot 34, to a fully extended position, wherein the shaft 28 has only about 17 mm of its length within the main body 12 and the slide tightening screw 32 is at a distal end of its slide slot 34. Workers skilled in the art will appreciate that different lengths of shafts and different lengths of slide slots in the main body 12 can be used depending upon the length of longitudinal adjustment which is desired for each extension arm 14. However, these preferred dimensions keep the entire device quite stable even when the extension arm 14 is fully extended from the main body 12. Once the desired longitudinal location for the extension arm 14 is achieved, the slide tightening screw 32 can be tightened down against its slide slot 34 to prevent further longitudinal movement of the extension arm 14 relative to the main body 12.

Each thumb wheel 24 includes internal threads 36 which mate with external threads 38 on the shaft 28. With the threaded connection, the thumb wheel 24 can be located at any desired longitudinal position along the length of the shaft 28. The thumb wheel 24 includes a grip portion 40 of relatively wide diameter and a smaller axial extension 42. The axial extension 42 of the thumb wheel 24 is receivable in a cylindrical recess 44 of the main body 12. The axial extension 42 includes an annular recess 46 which receives a locking screw 48.

The locking screw 48 threads into a hole 50 on the main body 12 and intersects the longitudinal axis of the thumb wheel 24.

The locking screw 48 has three basic positions relative to the thumb wheel 24: a fully loosened, coarse adjustment position in which the thumb wheel 24 can be fully removed from the cylindrical recess 44, an intermediate fine adjustment position in which the locking screw 48 rides in the annular recess 46 to hold the thumb wheel 24 at a set longitudinal position relative to the main body 12 but in which the thumb wheel 24 can still freely rotate about its longitudinal axis, and a fully tightened locked position in which the thumb wheel 24 is locked against any movement relative to the main body 12. With the thumb wheel 24 at a distal end of the rod member 18, the locking screw 48 in its fully loosened, coarse adjustment position, and the slide tightening screw loosened, the rod member 18 can slide longitudinally into or out from the main body 12. Once a coarse sliding position is determined and selected, the thumb wheel 24 is rotationally advanced proximally until the axial extension of the thumb wheel 24 is received in the cylindrical recess 44, and the locking screw 48 is partially tightened into the annular recess 46 of the thumb wheel 24. With the locking screw 48 loosely in the annular recess 46, rotation of the thumb wheel 24 finely adjusts the longitudinal position of the rod member 18 relative to the main body 12.

The joint portion 20 of each extension arm 14 allows the extension arm 14 freedom to bend and move to various locations relative to the main body 12. For some applications, the joint may be a simple pin-type hinge, or may not provide any angular freedom at all. However, beyond the extendable length of the rod member 18 relative to the main body 12, the preferred secureable joint 20 includes three additional degrees of adjustable freedom, each separately securable.

In the preferred embodiment, the joint 20 of the extension arm 14 is provided by the head 26 of the rod member 18, an intermediate universal connector 52, and ahead 54 of a pin holder support 56. The head 26 of the rod member 18 includes a threaded hole 58 for receiving a first joint bolt 60, with radially extending teeth 62 projecting around the bolt hole 58. The head 54 of the pin holder support 56 likewise includes a threaded hole 64 for receiving a second joint bolt 66, with radially extending teeth 62 projecting around the joint bolt hole 64. The intermediate universal connector 52 includes two bolt through holes 68, with mating radially extending teeth 62 around each of the joint bolt through holes 68. When the first joint bolt 60 is loosely engaged in the head 26 of the rod member 18, the intermediate universal connector 52 can pivot about the axis of the first joint bolt 60 as shown by arrow 70. Tightening of the first joint bolt 60 locks the intermediate universal connector 52 relative to the rod member 18 due to the interlocking engagement of the mating teeth 62. When the second joint bolt 66 is loosely engaged in the head 54 of the pin holder support 56, the pin holder support 56 can pivot about the axis of the second joint bolt 66 as shown by arrow 72. Tightening of the second joint bolt 66 locks the pin holder support 56 relative to the intermediate universal connector 52 due to the interlocking engagement of the mating teeth 62. Two degrees of adjustment freedom are thus provided by the pivoting allowed about each of the joint bolts 60, 66.

The third degree of adjustment freedom is provided because pin holder 22 rotationally attaches on a distal peg projection 74 of the pin holder support 56. A locking screw 76 extends through a threaded hole 78 in the pin holder 22 to intersect with an annular recess 80 on the pin holder support 56. With the locking screw 76 loosened, the pin holder support 56 can rotate about the axis of the distal peg projection 74 as shown by arrow 82. When the locking screw 76 is tightened, the rotational position of the pin holder 22 relative to the pin holder support 56 is fixed. Further, the locking screw 76 can be fully loosened to permit the pin holder 22 to be readily removed from the pin holder support 56.

The pin holder 22 includes two through holes 84 for receiving a transcutaneous bone attachment device (not shown) such as a bone screw, or more preferably a K-wire. Set screws 86 are provided for each of the K-wire through holes 84. The set screws 86 threadably attach into set screw holes 88 on the pin holder support 56, such that the axis of each set screw 86 intersects the axis of its K-wire through hole 84. If desired, additional openings or through holes may be provided in the pin holder 22 to give the surgeon additional options in securing the pin holder 22 relative to the bone or other tissue being secured.

A distal bolt hole 90 is provided along the longitudinal axis of the pin holder 22. A fixation member, which in the preferred embodiment is a ring 16, includes a bolt through hole 92 for a distal attachment bolt 94. Tightening of the distal attachment bolt 94 fixes the ring 16 relative to the pin holder 22.

The device 10 can alternatively be used without the three minor bodies 22 depending on the spanning length necessary to achieve the desired result. In particular, the distal peg projection 74 can be formed with an axial threaded bolt hole (not shown) similar to the distal bolt hole 90, enabling the distal peg projection 74 of the pin holder support 56 to be attached directly to the fixation ring 16.

The preferred fixation ring 16 is best shown in FIGS. 1-4. The fixation ring 16 include tracks 96 on both sides for receiving further pin holders (not shown) such as in the outrigger track taught in U.S. Pat. Nos. 6,652,524, 6,746,448 and pending application Ser. No. 10/699,313, incorporated by reference. The preferred fixation ring 16 extends for a 180° wrap angle 98 around the site of the bone intended to be fixed. The preferred fixation ring 16 has an inner diameter of about 130 mm or more so as to be sized to fit around large long bones, such as radius, ulna, humerous, tibia, fibula, ankle, hind foot, knee or even the distal femur. Other sizes of fixation ring 16 could be alternatively used for these or other anatomical fixation sites. The preferred fixation ring 16 includes an inner flange 100 and an outer flange 102 which define tracks 96 on both sides of a center web 104. The device 10 can be used with or without the fixation ring 16, depending upon whether fixation ring 16 proves useful in supporting k-wires, or other devices used to interact with the bone for the specific fracture being treated.

Figure 5:
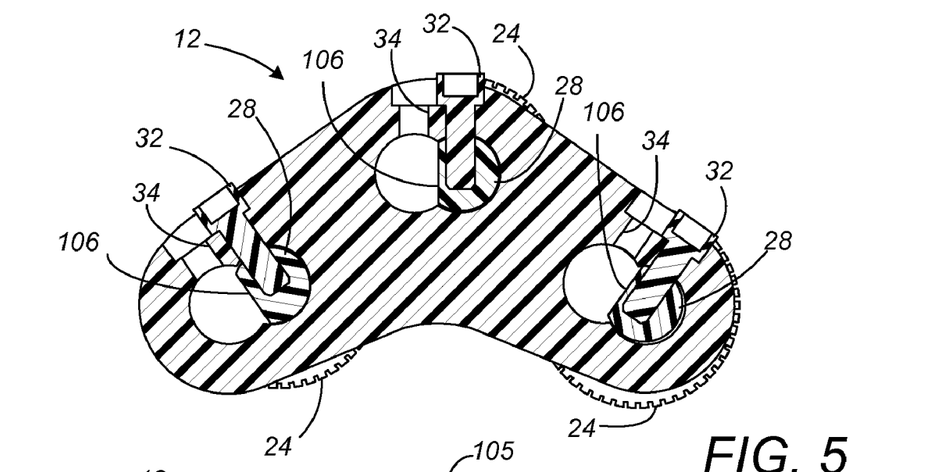
FIG. 5 is a cross-sectional view of the external fixator taken along line 5-5 of FIG. 1.
Figure 6:
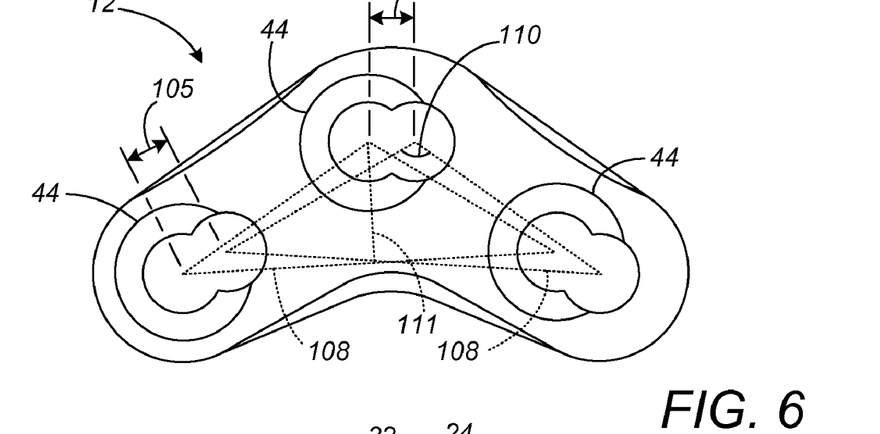
FIG. 6 is a side view of the main body of the external fixator of FIG. 1.
Figure 7:
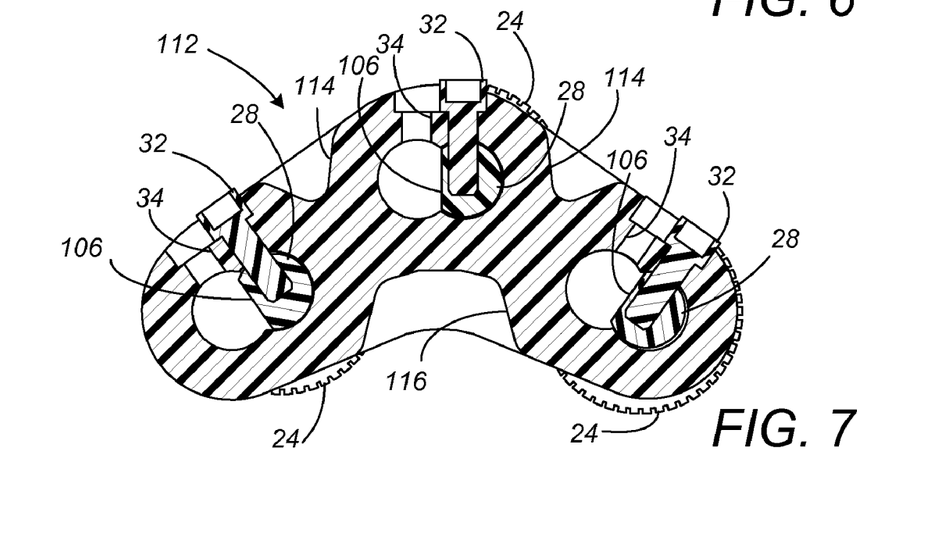
FIG. 7 is a cross-sectional view of an alternative external fixator having the same operative dimensions as the external fixator of FIG. 1.
Figure 8:
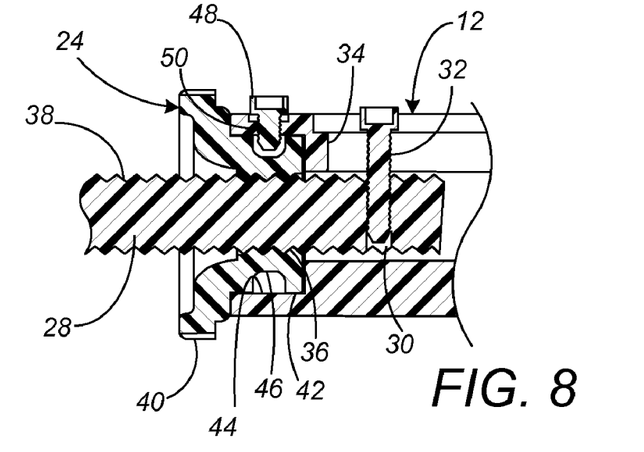
FIG. 8 is a cross-sectional view showing one of the thumb wheels captured by its set screw.

FIGS. 5-7 show the spatial relationship between the six rod members 18 in the main body 12. In particular, each rod member 18 is offset by an offset distance 105 relative to the rod member 18 on the opposing side, so the rod members 18 do not interfere with each other during retraction into the main body 12. With this arrangement, each rod member 18 can be either fully retracted or fully extended without interference from any of the other rod members 18. To minimize the offset distance 105 of the rod members 18 on opposing sides of the main body 12 and increase the balanced feel of the fixator device 10 as a whole, the main body 12 defines three slide chambers, with each slide chamber holding two abutting shafts 28. To further minimize the offset distance 105 of the rod members 18 on opposing sides of the main body 12 and further increase the balanced feel of the fixator device 10 as a whole, each rod member 18 includes a flat 106 which abuts against a corresponding flat 106 of the opposing rod member 18. An alternative configuration could use telescoping rod members, with one of the rod members acting as a tube for the other rod member. With telescoping rod members, the opposing rod members can utilize aligned longitudinal axes without the need for any offset. Another alternative configuration that utilizes aligned longitudinal axes without the need for any offset simply involves making a longer main body, with the shafts from opposing rod members contacting each other at their proximal ends when opposing shafts are fully retracted.

FIG. 6 includes dashed lines 108 showing the layout of the longitudinal axes of the six extension arms 14 relative to the main body 12. The six extension arms 14 are provided in two sets of three, with one set extending off each side of the main body 12. Each set of three extension arms 14 are arranged in a triangle 108, with the dimensions of the triangle 108 defining the wrap angle 110 for the extension arms 14 around the bone and defining the moment arms for supporting the fixation ring 16. The exact amount of wrap angle 110 and the exact amount of distance separating the longitudinal axes in the triangle 108 can be selected as necessary for the expected use of the fixation device 10. The preferred configuration provides a circumferential wrap angle 110 around the long bone of at least 30°, and more preferably a wrap angle 110 around the long bone of 60° or more. The preferred configuration also provides sufficient separation between the vertices of the triangle 108 that a minimum moment arm 111 of force through each vertex relative to the other two is at least about 10 mm, and more preferably 20 mm or more.

In the preferred embodiment, the triangle layout 108 provides a wrap angle 110 of about 66°, with the longitudinal axis of the center extension arm 14 spaced about 37 mm apart from each of the longitudinal axes of the side extension arms 14. The two side extension arms 14 are spaced with their longitudinal axes about 62 mm apart from each other. With this arrangement, the center extension arm 14 is about 34 mm above the base of the triangle 108, i.e., the minimum moment arm 111 supporting a twisting force on the fixation ring 16 is 34 mm.

FIG. 7 depicts an alternative embodiment of a main body 112. The main body 112 includes two recesses 114 on its top side and an additional recess 116 on its bottom side.

The recesses 114, 116 reduce the amount of thermoplastic material required and accordingly reduce the weight of the main body 112. The recesses 114, 116 also provide a more uniform wall thickness to the main body 112, so the main body 112 shrinks more uniformly in the molding process during solidification and is less like to warp or bend during molding. The recesses 114, 116 are provided in areas that do not significantly reduce the strength of the main body 112.

Figure 9:
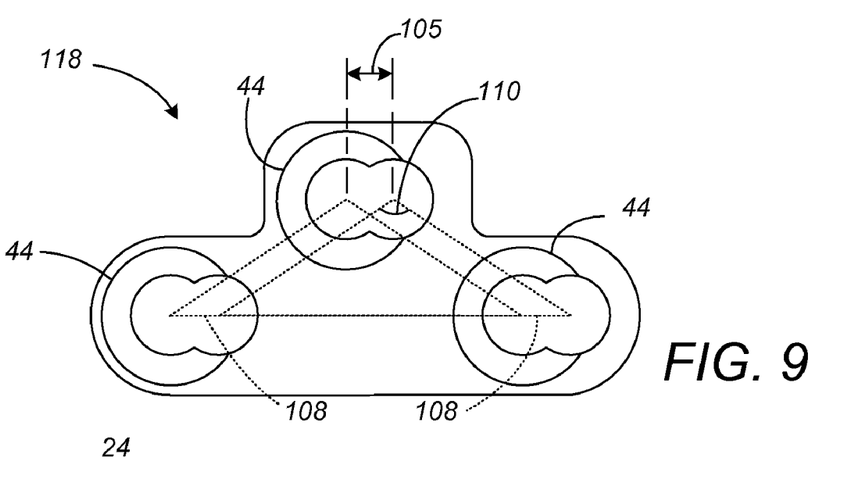
FIG. 9 is a side view of the main body of a second alternative preferred embodiment of an external fixator in accordance with the present invention.

FIG. 9 depicts another alternative embodiment, in which there is no angular offset between opposing rod members as defined in the main body 118, but merely a horizontal offset. The main body 118 of this design is particularly useful in situations wherein the axis of the long bone on one side of the fixator has an offset with the axis of the long bone on the other side of the fixator, e.g., wherein the bone structure has an offset which is comparable to the offset 105 of the main body 118.

Figure 10:
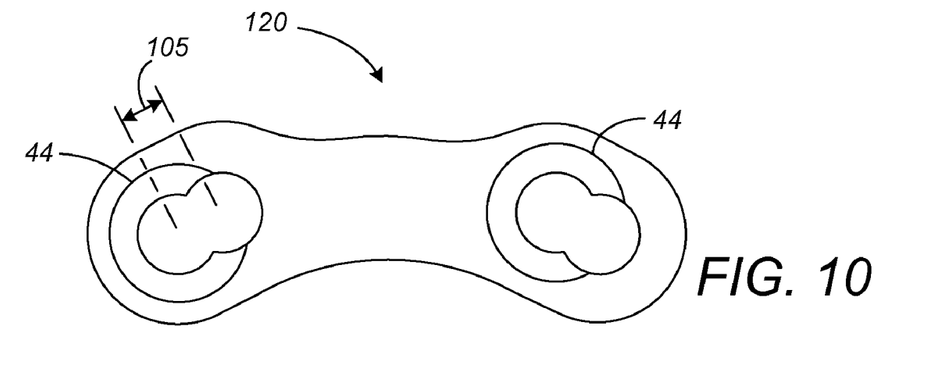
FIG. 10 is a side view of the main body of a third alternative preferred embodiment of an external fixator in accordance with the present invention.
Figure 11:
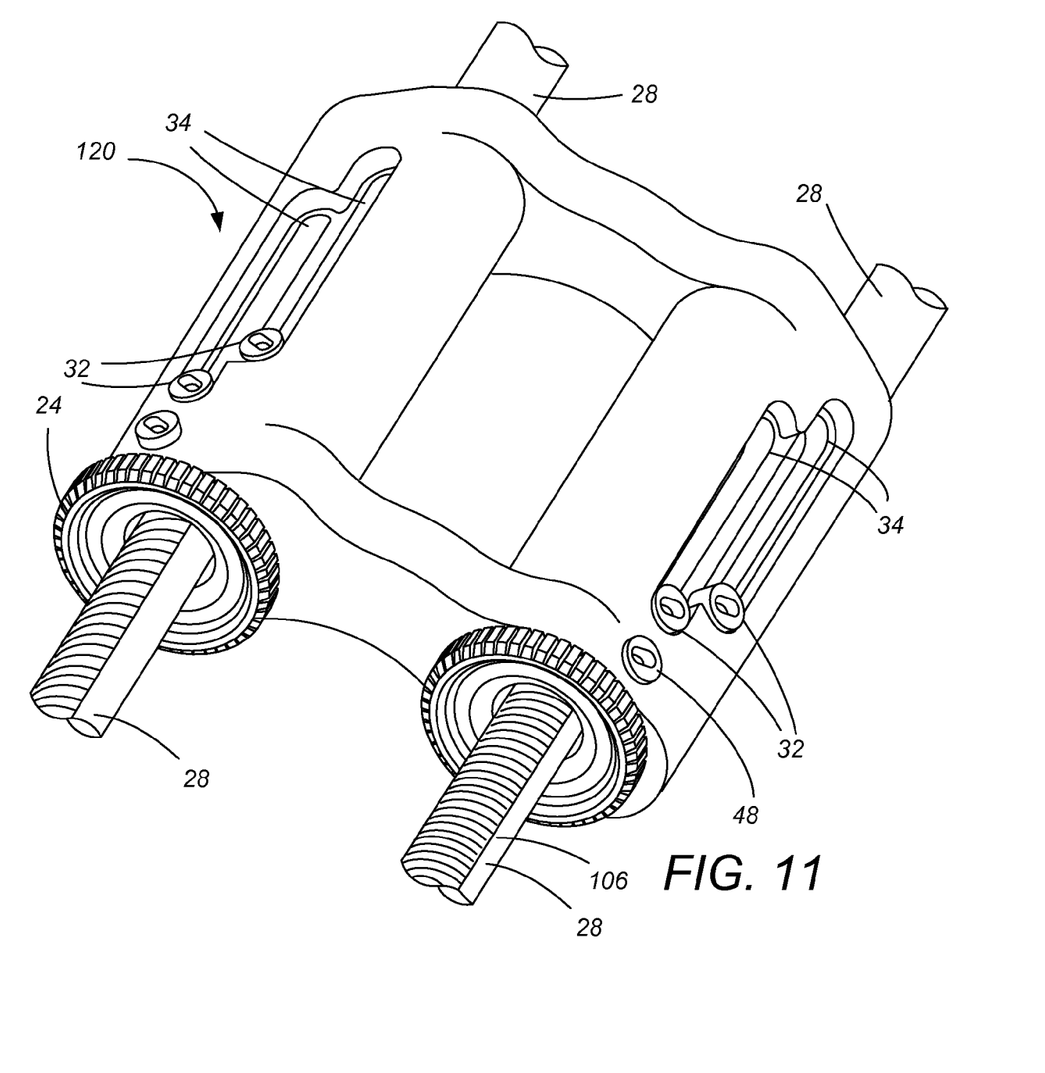
FIG. 11 is a perspective view of the external fixator of FIG. 10.

FIGS. 10 and 11 depict another alternative embodiment, in which only two sets of extension arms are used, and thus only four shafts 28 are present. The main body 120 of this design has an opening in the middle, providing an access location in the main body 120 between the two sets of four shafts 28. Including only two "tracks" (i.e., two sets or chambers each housing two shafts 28) reduces the cost and complexity of the main body 120. If desired, each shaft 28 may be rotationally coupled directly to a pin holder 10, with the joints 14 and ring 16 omitted, further reducing the cost and complexity of the fixator.

In this dual track embodiment, thumb wheels 24 are present only on one side of the main body 120. Thus, while both sets of shafts 28 can be extended or retracted in a coarse adjustment, only two of the shafts 28 can be extended or retracted in a fine adjustment. The use of thumb wheels 24 only on one side of the main body 120 still enables fine adjustment of the traction force, while reducing the cost and complexity of the fixator. Of course, the main body 120 of this dual track embodiment could be alternatively formed thumb wheels 24 for each shaft 28, just as the triple track fixator could be alternatively formed with thumb wheels 24 only on one side of the fixator 10.

Use of the fixator device 10 is straight forward and intuitive in numerous different settings. Transcutaneous bone pins or other tissue securing devices are set into the bone, bone fragment or other tissue being fixed. Preferred bone fasteners (not shown) are 3 mm bone pins or "K-wires", but many other types of bone fasteners (such as relatively long, thin bone screws, etc.) could equivalently be used. The bone pins may be affixed into the bone (reamed, driven, compression or distraction, etc.) as taught in U.S. Pat. Nos. 6,056,748, 6,283, 964, 6,652,524, 6,746,448 and pending application Ser. No. 10/699,313. Such bone fasteners can be surgically set in a hospital environment, but the fixator 10 of the present invention provides particular benefits in situations where the bone fasteners are set as soon as possible after the injury, such as in the field, or in an ambulance environment, or on an outpatient basis.

With the bone pins set as desired for any particular fracture, the fixator 10 of the present invention can be quickly modified to match the bone pin configuration. One or both pin holes 84 in the pin holder 22 can be used to receive one or more of the bone pins. Additional flexibility is provided by the fixation ring 16. Both with the fixation ring 16 and with the three pin holders 22, the configuration gives a significant amount of wrap 98, 108 around the bone location being fixed. The universal joint attachment with three points permits the fixation ring 16 to be placed at a wide variety of angular orientations relative to the main body 12. The configuration of the fixator 10 can be rapidly secured without use of the thumb wheels 24.

Each pin holder 22 (if used), and each fixation ring 16 (if used alternatively or in conjunction with the pin holders 22) is secured relative to the bone pins with set screws 86. Once the desire angular orientation of the fixation rings 16 and pin holders 22 is achieved, the orientations can be fixed by tightening of the first and second joint bolts 60, 66. The extension length of each of the extension arms 14 can be quickly fixed by tightening of the slide tightening screw 32. Alternatively, if either fine adjustment or control or a traction force is desired, then the thumb wheel 24 is rotationally advanced into the main body 12 and the wheel locking screw 48 is partially tightened. The distal (coarse adjustment) wheel locking screws 48 for each rod member 18 are tightened sufficiently into the annular recess 46 (visible at the top of FIG. 15) on the thumb wheels 24, preventing each rod member 18 from sliding without rotation of the thumb wheel 24. The thumb wheel 24 is then rotated to apply a traction force or to change the amount of axial extension of any particular one of the extension arms 14.

Of particular importance, the fixator 10 of the present invention allows a coarse setting in the field at one time, followed at a later time, perhaps by different personnel, with fine adjustment or application of a traction force. The fixator 10 is lightweight and strong enough that it can further be used while the patient is gaining mobility and during healing of the bone. Thus the same fixator 10 can be used from start to finish during the healing process, set in the field, adjusted by the surgeon, and worn by the patient throughout healing. It utilizes a single housing 12 having a plurality of parallel shafts 28 which are each independently longitudinally extendable to set a desired angular orientation of the fixation ring 16 on an end of the device 10. The fixator 10 enables medical field personnel or a surgeon or to use the same fixator 10 both to immobilize a fractured limb and later to set the fractured bone with desired traction on the fracture.

In contrast with many prior art fixator devices, each of the component parts of the preferred fixator 10 can be formed of a molded thermoplastic material, with the preferred material being ULTEM. Forming the fixator 10 out of molded thermoplastic components reduces the cost of manufacture of the fixator 10 and reduces the weight of the fixator 10. A significantly lower cost of the fixator 10 is very important in enabling the fixator 10 to be distributed in sterile, sealed packaging for single use, disposable applications. A lower weight of the fixator is important not only for the patient wearing the fixator 10, but also for shipping the fixator 10, particularly if tens or hundreds of fixators 10 are jointly transported such as for large hospital or military applications. Forming the fixator 10 out of molded thermoplastic also makes the fixator 10 translucent to x-rays and many imaging techniques, so the fixator 10 does not interfere with further imaging of the fracture site.

The additional benefits and attributes of the fixator 10 device are many. The hemispheric, uni-body design allows for rapid, intuitive, adjustable fixation. The hemispheric, angulated, uni-body design affords the surgeon maximum access to the fracture site, and provides a maximum range of correctablity and adjustability. The design allows for three point, multi planar fixation both distally and proximally. The circular fixation achieved by the present invention is provided in a modular package that is easier to affix to a patient as a result of adjustability options. The single body/frame 12 with multiple fixation arms 14 allows for multiple planes of fixation without the need for multiple rings 16, though rings 16 can be used if desirable.

Although the present invention has been described with reference to preferred embodiments, workers skilled in the art will recognize that changes may be made in form and detail without departing from the spirit and scope of the invention.

The invention claimed is:

1. An external fixator for attachment to a bone comprising:
a main body defining a longitudinal direction;
a rod extending longitudinally out of the main body, the rod having a coarse longitudinal position adjustment capability relative to the main body and having a fine longitudinal position adjustment capability relative to the main body;
a slide channel for coarse sliding adjustment of the longitudinal position of the rod;
a set screw extending through the main body for fixing the coarse sliding adjustment of the rod; a thumb wheel for fine threaded rotational adjustment of the longitudinal position of the rod; and
a set screw extending through the main body for engaging the thumb wheel and fixing the fine threaded rotational adjustment of the rod.

2. An external fixator device comprising:
a main body defining a longitudinal direction;
three parallel shafts supported by the main body each having a primary axis extending in the longitudinal direction, each of the shafts being independently longitudinally adjustable relative to the main body, the three shafts being configured to support one or more bone attachment devices; and
a connection body attachable to distal ends of all three shafts, with the angular position of the connection body being selectable based upon the longitudinal position of each of the three shafts.

3. The external fixator device of claim 2, wherein the three parallel shafts are supported by the main body in a non-planar configuration.

4. The external fixator device of claim 2, wherein the connection body attaches to the three shafts with three universal joints, one universal joint for each shaft.

5. An external fixator device comprising:
a main body defining a longitudinal direction between a first side and an opposing second side;
three parallel shafts supported by the main body each having a primary axis extending in the longitudinal direction, each of the shafts being independently longitudinally adjustable relative to the main body, the three shafts being configured to support one or more bone attachment devices, wherein the three parallel shafts extend off the first side of the main body, and
an additional three parallel shafts extending off the opposing second side of the main body.

6. An external fixator for attachment to a bone comprising:
a main body defining a longitudinal direction;
a fixation body which is angularly adjustable relative to the main body;
first, second and third connections between the main body and the fixation body each separately connecting the main body to the fixation body, each of the first, second and third connections being independently longitudinally adjustable toward and away from the main body;
wherein the first connection defines a first connection point on the fixation body;

wherein the second connection defines a second connection point on the fixation body, the second connection point being spaced by at least 10 mm from the first connection point; and wherein the third connection defines a third connection point on the fixation body, the third connection point being spaced by at least 10 mm from a line running from the first connection point to the second connection point.

7. The external fixator of claim 6, wherein each of the first, second and third connections is capable of supporting a compression or tension force between the fixation body and the main body.

8. The external fixator of claim 6, wherein each of the first, second and third connections is jointed to permit angular adjustment of the fixation body relative to the main body.

9. The external fixator of claim 6, wherein the fixation body is securable at different angular positions relative to the main body such that the fixation body is able to support moments in any direction relative to the main body based upon the compression or tension forces at the first, second and third connections acting through moment arms defined by the spacing between the first, second and third connections.

10. An external fixator for attachment to a bone comprising:
 a main body defining a longitudinally extending slide chamber running between a proximal end and a distal end.
 a first extension rod projecting out the proximal end of the slide chamber, the first extension rod being longitudinally extendable out of and longitudinally retractable into the slide chamber; and
 a second extension rod projecting out the distal end of the slide chamber, the second extension rod being longitudinally extendable out of and longitudinally retractable into the slide chamber independent of the longitudinal extension of the first extension rod.

11. An external fixator for attachment to a long bone comprising:
 a main body defining a longitudinal direction generally parallel to the longitudinal axis of the long bone;
 a first support longitudinally extending from the main body along a first support longitudinal axis generally parallel to the longitudinal axis of the long bone, the first support being adapted to hold at least one first pin or screw embedded in the long bone; and
 a second support longitudinally extending from the main body along a second support longitudinal axis generally parallel to the longitudinal axis of the long bone and generally parallel to the first support longitudinal axis, the second support being adapted to hold at least one second pin or screw embedded in the long bone;
 wherein both the first and second support are independently longitudinally adjustable for extension and retraction relative to the main body, wherein extending the first and second supports positions the first pin or screw and second pin or screw further from the main body, and wherein retracting the first and second supports positions the first pin or screw and second pin or screw nearer the main body;
 wherein the second support longitudinal axis is spaced from the first support longitudinal axis by a wrap angle around the long bone, the second support being adapted to hold at least one second pin or screw embedded in the long bone and circumferentially spaced at a wrap angle around the long bone of at least 60° relative to the first pin or screw.

12. The external fixator of claim 11, wherein extending the first and second supports positions the first pin or screw and second pin or screw further from each other, and wherein retracting the first and second supports positions the first pin or screw and second pin or screw nearer to each other.

* * * * *